US009833258B2

(12) United States Patent
Kusleika

(10) Patent No.: US 9,833,258 B2
(45) Date of Patent: *Dec. 5, 2017

(54) MATERIAL REMOVAL DEVICE AND METHOD OF USE

(71) Applicant: Covidien LP, Mansfield, MA (US)

(72) Inventor: Richard S. Kusleika, Eden Prairie, MN (US)

(73) Assignee: Covidien LP, Mansfield, MA (US)

( * ) Notice: Subject to any disclaimer, the term of this patent is extended or adjusted under 35 U.S.C. 154(b) by 5 days.

This patent is subject to a terminal disclaimer.

(21) Appl. No.: 15/139,859

(22) Filed: Apr. 27, 2016

(65) Prior Publication Data

US 2016/0317181 A1 Nov. 3, 2016

Related U.S. Application Data

(63) Continuation of application No. 13/740,609, filed on Jan. 14, 2013, now Pat. No. 9,351,757.

(Continued)

(51) Int. Cl.
*A61B 17/22* (2006.01)
*A61B 17/3207* (2006.01)
(Continued)

(52) U.S. Cl.
CPC ............... *A61B 17/320758* (2013.01); *A61B 17/320783* (2013.01); *A61B 2017/00734* (2013.01); *A61B 2017/2913* (2013.01); *A61B 2017/320024* (2013.01); *A61B 2017/320032* (2013.01); *A61B 2017/320716* (2013.01);
(Continued)

(58) Field of Classification Search
CPC .... A61B 17/320758; A61B 17/320783; A61B 2017/2913; A61B 2017/320024; A61B 2017/320032; A61B 2017/320716; A61B 2017/320733; A61B 2017/320791; A61B 2019/4805; A61B 2019/528
See application file for complete search history.

(56) References Cited

U.S. PATENT DOCUMENTS 4,781,181 A 11/1988 Tanguy
4,994,067 A 2/1991 Summers
(Continued)

FOREIGN PATENT DOCUMENTS

EP 1595503 11/2005
WO WO2006011970 2/2006
(Continued)

*Primary Examiner* — Ashley Fishback

(57) ABSTRACT

A catheter having a tubular body and a rotatable shaft disposed within a lumen of the tubular body. A cutting element is coupled to the rotatable shaft, the cutting element having a cutting edge, the cutting element and rotatable shaft being longitudinally moveable within the tubular body between a stored position in which the cutting element is parallel a longitudinal axis of the tubular body and a cutting position in which the cutting element is deflected between the proximal and distal ends of the tubular body to extend beyond an outer diameter of the tubular body. The cutting element is configured to cut material from the wall of a vessel at a treatment site as the catheter is pushed distally through the treatment site. The catheter includes a collection chamber positioned proximally of the cutting window.

13 Claims, 9 Drawing Sheets

Related U.S. Application Data

(60) Provisional application No. 61/587,369, filed on Jan. 17, 2012.

(51) Int. Cl.
| | | |
|---|---|---|
| A61B 17/29 | (2006.01) | |
| A61B 17/32 | (2006.01) | |
| A61B 90/00 | (2016.01) | |
| A61B 17/00 | (2006.01) | |

(52) U.S. Cl.
CPC ............ *A61B 2017/320733* (2013.01); *A61B 2017/320791* (2013.01); *A61B 2090/0801* (2016.02); *A61B 2090/3784* (2016.02)

(56) References Cited

U.S. PATENT DOCUMENTS

| | | | |
|---|---|---|---|
| 5,133,725 A | 7/1992 | Quadri | |
| 5,224,949 A | 7/1993 | Gomringer et al. | |
| 5,507,795 A | 4/1996 | Chiang et al. | |
| 5,632,754 A | 5/1997 | Farley et al. | |
| 5,899,915 A | 5/1999 | Saadat | |
| 6,299,622 B1 | 10/2001 | Snow et al. | |
| 6,623,496 B2 | 9/2003 | Snow et al. | |
| D480,807 S | 10/2003 | Yardan et al. | |
| 6,830,545 B2 | 12/2004 | Bendall | |
| 7,018,390 B2 | 3/2006 | Turovskiy et al. | |
| 7,223,230 B2 | 5/2007 | Zirps et al. | |
| 7,326,224 B2 | 2/2008 | Houde et al. | |
| 7,708,749 B2 | 5/2010 | Simpson et al. | |
| 7,789,825 B2 | 9/2010 | Nobis et al. | |
| 7,862,518 B2 | 1/2011 | Parihar | |
| 8,128,647 B2 | 3/2012 | Kennedy | |
| 2003/0018346 A1 | 1/2003 | Follmer et al. | |
| 2003/0125757 A1 | 7/2003 | Patel et al. | |
| 2005/0222663 A1 | 10/2005 | Simpson et al. | |
| 2007/0016071 A1* | 1/2007 | Eberle | A61B 8/06 600/468 |
| 2008/0004643 A1 | 1/2008 | To et al. | |
| 2009/0187203 A1 | 7/2009 | Corvi et al. | |
| 2009/0270897 A1 | 10/2009 | Adams et al. | |
| 2010/0130850 A1 | 5/2010 | Paktor | |
| 2011/0130777 A1 | 6/2011 | Zhang et al. | |
| 2011/0144673 A1 | 6/2011 | Zhang et al. | |
| 2011/0166575 A1 | 7/2011 | Assell et al. | |
| 2011/0270256 A1 | 11/2011 | Nelson | |
| 2011/0306995 A1 | 12/2011 | Moberg | |
| 2014/0371718 A1* | 12/2014 | Alvarez | A61M 25/0074 604/510 |

FOREIGN PATENT DOCUMENTS

| | | |
|---|---|---|
| WO | WO2006105244 | 10/2006 |
| WO | WO2007130711 | 11/2007 |
| WO | WO2010045226 | 4/2010 |
| WO | WO2010132748 | 11/2010 |
| WO | WO2011112918 | 9/2011 |
| WO | WO2011159697 | 12/2011 |
| WO | WO2012003430 | 1/2012 |

\* cited by examiner

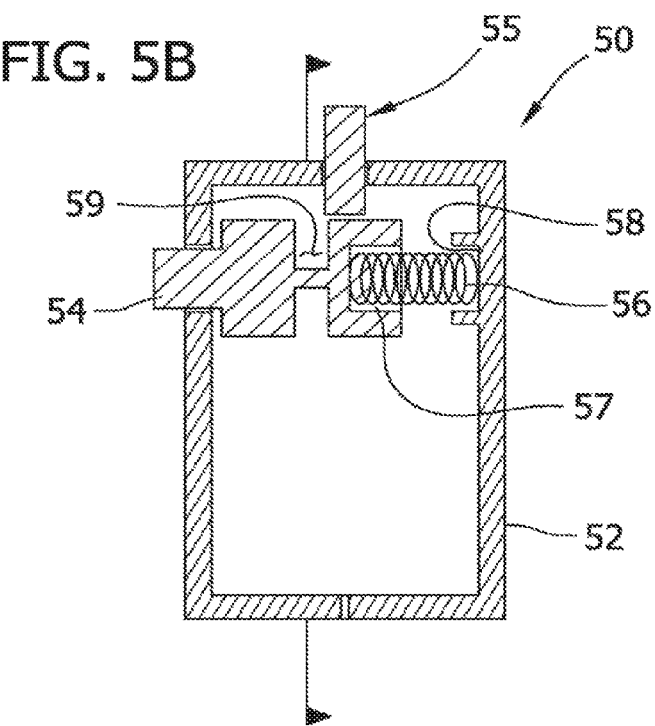
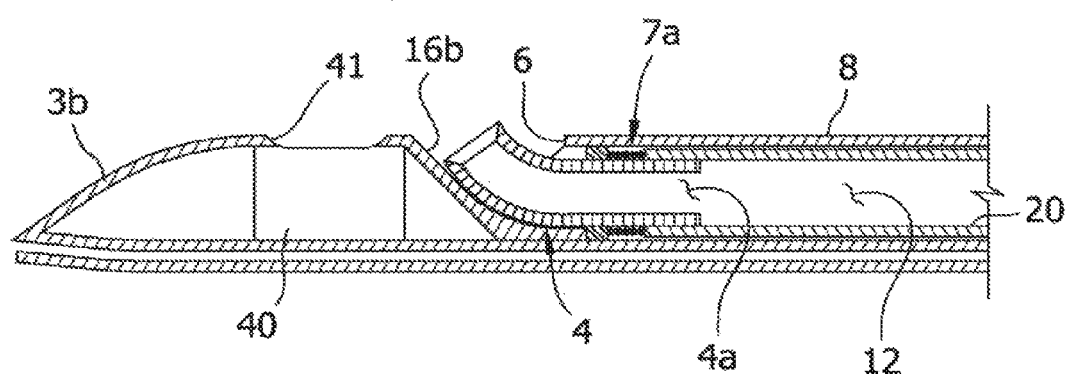

MATERIAL REMOVAL DEVICE AND METHOD OF USE

CROSS-REFERENCE TO RELATED APPLICATIONS

The present application is a continuation of U.S. application Ser. No. 13/740,609, filed Jan. 14, 2013, now U.S. Pat. No. 9,351,757, which claims priority to U.S. Provisional Application Ser. No. 61/587,369, filed Jan. 17, 2012, the entirety of which is incorporated by reference herein.

FIELD OF THE INVENTION

The present invention relates to catheters used to remove and collect material from a treatment site in a body lumen. More particularly, this invention pertains to atherectomy catheters for treating vascular disease.

BACKGROUND OF THE INVENTION

Atherosclerosis is a progressive disease of the vascular system whereby atheroma is deposited on the inner walls of blood vessels. Atherosclerosis is a complex degenerative condition resulting in the build-up of cholesterol, calcium, and other obstructive materials, known as plaque, on the walls of the arteries. The accumulation of plaque narrows the interior lumen of arteries, thereby reducing blood flow.

Plaque occurs in the arteries in several different forms and may be located in many different anatomies throughout the arterial system. Plaque varies in composition, with portions that are hard and brittle, referred to as calcified plaque, and other portions that are fatty or fibrous. Over time atheromatous deposits can become large enough to reduce or occlude blood flow through the vessels, leading to symptoms of low blood flow, such as claudication (pain in the legs on walking or at rest), skin ulcer, critical limb ischemia, and other symptoms. To treat this disease and improve or resolve these symptoms it is desirable to restore or improve blood flow through the vessel.

Various means are used to restore or improve blood flow through atheromatous vessels. The atheroma deposits can be displaced by diametrically expanding the vessel by inflating balloons, expanding stents, and other methods. The deposits can be fragmented using lasers and other methods. Atherectomy catheters can be used to remove atheromatous deposits from the blood vessel.

Many types of atherectomy catheter devices have been proposed, including catheters with rotating burrs, lasers to photodissolve tissue, and cutter-balloon catheters. The various catheter embodiments described herein incorporate improvements with respect to the structure of the catheters and methods of use and manufacture.

SUMMARY OF THE INVENTION

Various catheter embodiments, optional features, and methods of use and manufacture are disclosed herein. Distinguishing features that may be included in these catheter embodiments and methods are described below in connection with specific embodiments or methods. It is intended that the catheters and methods described herein may include one or more of these features, individually or in combination, and it is not intended that this disclosure be limited to the specific combination of features described in connection with the embodiments or methods disclosed herein.

In one embodiment, a catheter for removing material from a body lumen generally comprises a tubular body having proximal and distal ends, a longitudinal axis, a side opening adjacent the distal end of the tubular body, and a lumen extending along the longitudinal axis of the body; a rotatable shaft disposed within the lumen of the tubular body and having proximal and distal ends and a longitudinal axis extending between its proximal and distal ends; a ramp coupled to the tubular body adjacent the distal end of the body and having an angular surface generally opposite the side opening; and a flexible cutting element having proximal and distal ends, a longitudinal axis extending between its proximal and distal ends, and an axis of rotation extending between its proximal and distal ends, the proximal end of the cutting element being coupled to the rotatable shaft for imparting rotation of the cutting element about its axis of rotation, and the distal end of the cutting element having a cutting edge adapted to cut material from the body lumen. The cutting element and the rotatable shaft are longitudinally moveable within the tubular body between a stored position, in which the cutting element is received in the tubular body, and a cutting position, in which the cutting element engages the angular surface of the ramp and is deflected along its longitudinal axis such that at least a portion of the longitudinal axis of the cutting element is not parallel to the longitudinal axis of the tubular body and at least a portion of the cutting edge extends through the side opening.

The catheter may further include a biasing member coupled to the rotatable shaft and configured to bias the cutting element toward the stored position. The biasing member may include a stop coupled to the tubular shaft proximal the side opening and a retraction member coupled to the stop and the distal end of the rotatable shaft. As the cutting element is longitudinally extended from the stored position to the cutting position the retraction member is compressed creating a retraction force that retracts the cutting element from the cutting position to the stored position. The stop of the catheter may be a retraction ring and the retraction member may be a retraction spring.

The catheter may include that the rotatable shaft has a wall defining a lumen and the catheter may further include a material collection chamber positioned within the tubular body at a location proximal of the side opening. The catheter may include a nosecone distal the side opening, the nosecone housing an imaging transducer. The nosecone may further include a luminal wall and at least one slot and the imaging transducer may have 360° image capability of the vascular lumen through the luminal wall and slot of the nosecone. The catheter may further include a guidewire lumen extending along an outer surface of the tubular body.

The catheter may include a handle attached at a proximal portion of the tubular body, the handle including a power source, a motor coupled to the power source, and an cam follower coupled to the rotatable shaft, wherein the motor is configured to transmit rotation and distal movement to the cam follower and rotatable shaft when energized by the power source to thereby move the cutting element from the stored position to the cutting position. The handle may further include a cylindrical cam coupled to the motor, the cylindrical cam comprising a spiral slot configured to receive a projection from the cam follower, wherein rotation of the cylindrical cam by the motor longitudinally extends the projection of the cam follower within the spiral slot of the cylindrical cam from a starting position at a proximal end of the spiral slot to an extended position toward a distal end of the spiral slot thereby extending longitudinally the rotatable shaft and cutting element from the stored position to the cutting position.

The catheter may include a controller having a body defining a lumen sized to accept the tubular body, the controller further having opposed shaft engaging elements within the body, a lever and an activation member wherein the lever is movable into an engaged position whereby the shaft engaging elements engage the tubular body and engage the activation member in communication with the power source to energize the motor and a disengaged position whereby the body is free to rotate and axially translate over the elongate tubular shaft and communication is halted to the power source.

The catheter may include a rotatable shaft that is metallic and a portion of the rotatable shaft may be spirally cut. In another embodiment, a catheter generally comprises: a tubular body having proximal and distal ends and a side opening positioned proximal of the distal end of the tubular body; a rotatable shaft disposed within the lumen of the tubular body, the rotatable shaft having proximal and distal ends; a cutting element coupled to the rotatable shaft the cutting element having a cutting edge; a cam follower secured to the rotatable shaft adjacent the proximal end of the rotatable shaft; and a handle attached to the tubular body adjacent the proximal end of the tubular body, the handle including a motor, and a cylindrical cam coupled to the motor and to the cam follower. The cutting element and the rotatable shaft are longitudinally moveable within the tubular body between a stored position, in which the cutting element is received in the tubular body, and a cutting position, in which at least a portion of the cutting edge extends through the side opening. The motor is configured to transmit rotation to the cylindrical cam to both impart translation to the cam follower to move the cutting element from the stored position to the cutting position and impart rotation to the cam follower when the cutting element is in the cutting position to rotate the cutting element about its axis of rotation.

The cylindrical cam may have a spiral slot and the cam follower may have a projection and wherein rotation of the cylindrical cam by the motor longitudinally extends the rotatable shaft in the body by moving the projection of the cam follower within the spiral slot of the cylindrical cam from the starting position at a proximal end of the spiral slot to the extended position toward a distal end of the spiral slot thereby extending longitudinally the rotatable shaft from the stored position to the cutting position. The catheter may further include a biasing member coupled to the cylindrical cam configured to bias the cam follower in the starting position of the cylindrical cam thereby biasing the cutting element toward the stored position. The biasing member may have a stop coupled to the rotatable shaft and a retraction member coupled to the stop and the proximal end of the cylindrical cam. Compression of the retraction member creates a retraction force that returns the pin of the cam follower from the extending position within the spiral slot of the cylindrical cam to the starting position of the spiral slot of the cylindrical cam when rotation of the cylindrical cam is halted, thereby returning the cutting element from the cutting position to the stored position. The retraction member may be a retraction spring and the stop may be a nut.

The handle may include a cut depth controller coupled to the rotatable shaft to selectively control a distance in which the cutting edge extends beyond the outer diameter of the tubular body in the cutting position. The cut depth controller may have a nut having more than one slotted distance marker and a cut depth adjustment member having a movable lever wherein as the cut depth adjustment member is adjustably coupled unto the nut, the movable lever is accepted into one of the slotted distance markers. Each slotted distance marker marks a distance the cam follower will longitudinally extend thereby marking the distance the rotatable shaft and cutting element will longitudinally extend. The catheter may be configured such that the further the cut depth adjustment member is adjustably coupled unto the nut, the smaller the distance from the starting position of the cylindrical cam to the nut and the less the cam follower will longitudinally extend thereby marking the distance the rotatable shaft and cutting element will longitudinally extend.

The catheter may include a biasing member coupled to the cylindrical cam and the rotatable shaft and configured to bias the cam follower in the starting position of the cylindrical cam thereby biasing the cutting element toward the stored position. The catheter may be configured such that the compression of the biasing member creates a retraction force and wherein the retraction force returns the pin of the cam follower from the extending position within the spiral slot of the cylindrical cam to the starting position of the spiral slot of the cylindrical cam when rotation of the cylindrical cam is halted, thereby returning the cutting element from the cutting position to the stored position.

The catheter may include a nosecone distal the side opening, the nosecone housing an imaging transducer. The nosecone has a luminal wall and at least one slot and the imaging transducer has 360° image capability of the vascular lumen through the luminal wall and slot of the nosecone.

The catheter may include a controller having a body defining a lumen sized to accept the tubular body. The controller may further have opposed shaft engaging elements within the body, a lever and an activation member. The controller may be configured so that the lever is movable into an engaged position whereby the shaft engaging elements engage the tubular body and engage the activation member in communication with the power source to energize the motor and a disengaged position whereby the body is free to rotate and axially translate over the elongate tubular shaft and communication is halted to the power source.

In yet another embodiment, a method of removing material from a treatment site within a body lumen generally comprises advancing a catheter within the body lumen to a treatment site in the body lumen. The catheter includes a tubular body having proximal and distal ends, a longitudinal axis, a side opening adjacent the distal end of the tubular body, and a lumen extending along the longitudinal axis of the body, a rotatable shaft disposed within the lumen of the tubular body and having proximal and distal ends and a longitudinal axis extending between its proximal and distal ends, a ramp coupled to the tubular body adjacent the distal end of the body and having an angular surface generally opposite the side opening, and a flexible cutting element having proximal and distal ends, a longitudinal axis extending between its proximal and distal ends, and an axis of rotation extending between its proximal and distal ends, the proximal end of the cutting element being coupled to the rotatable shaft for imparting rotation of the cutting element about its axis of rotation, and the distal end of the cutting element having a cutting edge adapted to cut material from the body lumen. The method further comprises longitudinally moving the rotatable shaft and the cutting element within the tubular body after said advancing the catheter to move the cutting element from a stored position, in which the cutting element is received in the tubular body, to a cutting position, in which the cutting element engages the angular surface of the ramp and is deflected along its longitudinal axis such that at least a portion of the longitudinal axis of the cutting element is not parallel to the longitudinal axis of the tubular body and at least a portion of the cutting edge extends through the side opening. The catheter is advanced distally through the body lumen with the cutting element in the cutting position to move the cutting edge of the cutting element across the treatment site to cut material from the treatment site.

In another embodiment, a method of removing material from a treatment site within a body lumen generally comprises advancing a catheter within the body lumen to a treatment site in the body lumen. The catheter includes a tubular body having proximal and distal ends and a side opening positioned proximal of the distal end of the tubular body, a rotatable shaft disposed within the lumen of the tubular body, the rotatable shaft having proximal and distal ends, a cutting element coupled to the rotatable shaft, the cutting element having a cutting edge, a cam follower secured to the rotatable shaft adjacent the proximal end of the rotatable shaft, and a handle attached to the tubular body adjacent the proximal end of the tubular body, the handle including a motor, and a cylindrical cam coupled to the motor and to the cam follower. The motor is activated after said advancing the catheter to transmit rotation to the cylindrical cam to impart both i) translation to the cam follower to longitudinally move the shaft and the cutting element from a stored position, in which the cutting element is received in the tubular body, to a cutting position, in which at least a portion of the cutting edge extends through the side opening, and ii) rotation to the cam follower to rotate the shaft and the cutting element after moving the cutting element to the cutting position. The catheter is advanced distally through the body lumen with the cutting element in the cutting position to move the cutting edge of the cutting element across the treatment site to cut material from the treatment site.

The catheter of any of the above methods may include a biasing mechanism coupled to the rotatable shaft and configured to bias the cutting element toward the stored position. The method may include that the step of moving the cutting element from a stored position within the tubular body to an extended cutting position compresses the biasing mechanism and creates a retraction force. In this method the step of retracting the cutting element from the extended cutting position to the stored position may be performed by the retraction force created by the compression of the biasing mechanism wherein as the retraction force of the biasing mechanism is released the cutting element is longitudinally retracted.

The handle of the catheter of any of the above methods may be coupled to the proximal end of the tubular body, and may have a power source, a motor, and a cylindrical cam coupled to the motor. The cylindrical cam may have a spiral slot, and a cam follower coupled to the rotatable shaft. The cam follower may have a pin configured to be received within the spiral slot of the cylindrical cam.

The step of moving the cutting element from a stored position within the tubular body to an extended cutting position may be performed by rotation of the cylindrical cam moving the pin of the cam follower within the spiral slot of the cylindrical cam from a starting position at a proximal end of the spiral slot to an extended position toward a distal end of the spiral slot thereby extending longitudinally the rotatable shaft and extending a portion of the cutting element up an angular surface of a ramp opposite the side opening and extending the cutting edge through the side opening beyond an outer diameter of the tubular body.

The catheter of any of the above methods may include a cut depth controller coupled to the rotatable shaft. The method may include the step of selectively controlling a cutting depth in which the cutting edge extends beyond the outer diameter of the tubular body in the cutting position.

The cut depth controller of any of the above methods may include a cut depth adapter with a lever adjustably coupled to a nut having at least one slotted distance marker, the lever being configured to be received within the at least one slotted distance marker, the at least one slotted distance marker being configured to be a specific cutting depth of the cutting element. The catheter of the method may further include a gap between the proximal end of the cylindrical cam and a distal end of the nut, the gap having a length and wherein the biasing mechanism is coupled to the proximal end of the cylindrical cam and the distal end of the nut.

The step of selectively controlling a distance in which the cutting edge extends beyond the outer diameter of the tubular body in the cutting position further includes that the length of the gap is controlled by the adjustable coupling of the cut depth adapter to the nut and the receiving of the lever in the slotted distance marker, and as the pin of the cam follower moves within the spiral slot of the cylindrical cam from the starting position toward the extending position, the nut longitudinally extends toward the proximal end of the cylindrical cam and compresses the biasing mechanism. The step of selectively controlling a distance in which the cutting edge extends beyond the outer diameter of the tubular body in the cutting position further includes that the smaller the length of the gap, the smaller the cutting edge extends beyond the outer diameter of the tubular body in the cutting position.

The step of moving the cutting element from a stored position within the tubular body to an extended cutting position further includes that the compressing of the biasing mechanism creates a retraction force. The step of retracting the cutting element from the extended cutting position to the stored position may be performed by the retraction force created by the compression of the biasing mechanism wherein as the rotation of the cylindrical cam is halted the retraction force of the biasing mechanism is released retracting the pin of the cam follower from the extending end of the spiral slot to the starting end of the spiral slot.

These and other aspects of the invention will become apparent from the following description of the preferred embodiments, drawings and claims. The details of one or more embodiments of the invention are set forth in the accompanying drawings and the description below. Other features, objects, and advantages of the invention will be apparent from the description and drawings, and from the claims.

Figure 2A:
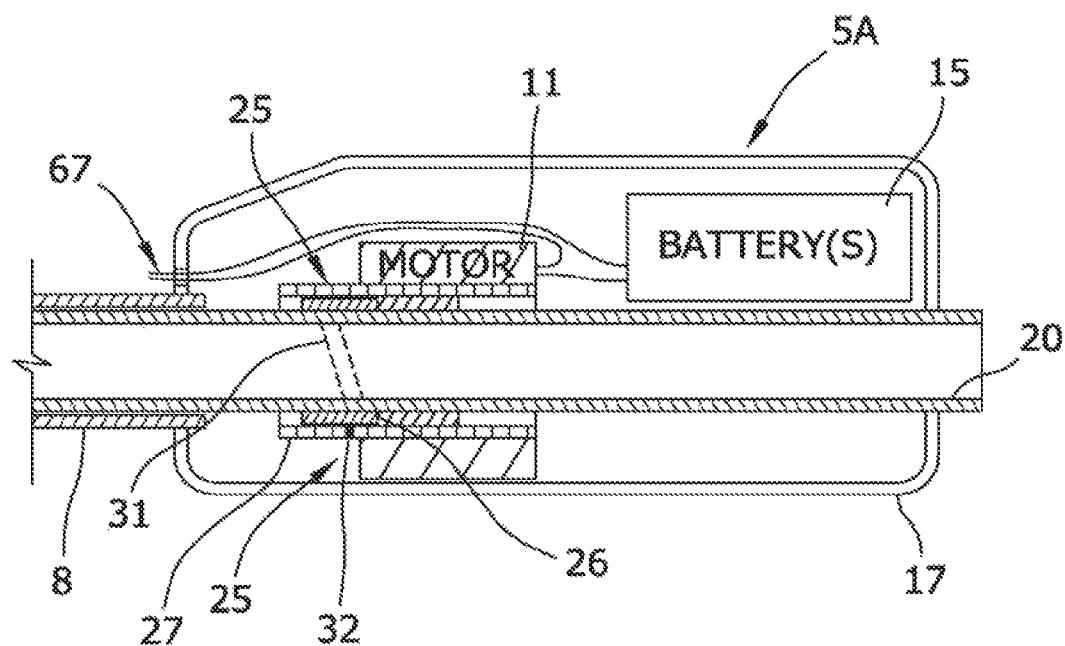
FIG. 2A is a schematic, fragmentary side cross-sectional view of a cutter driver of the atherectomy catheter of FIGS.
Figure 2B:
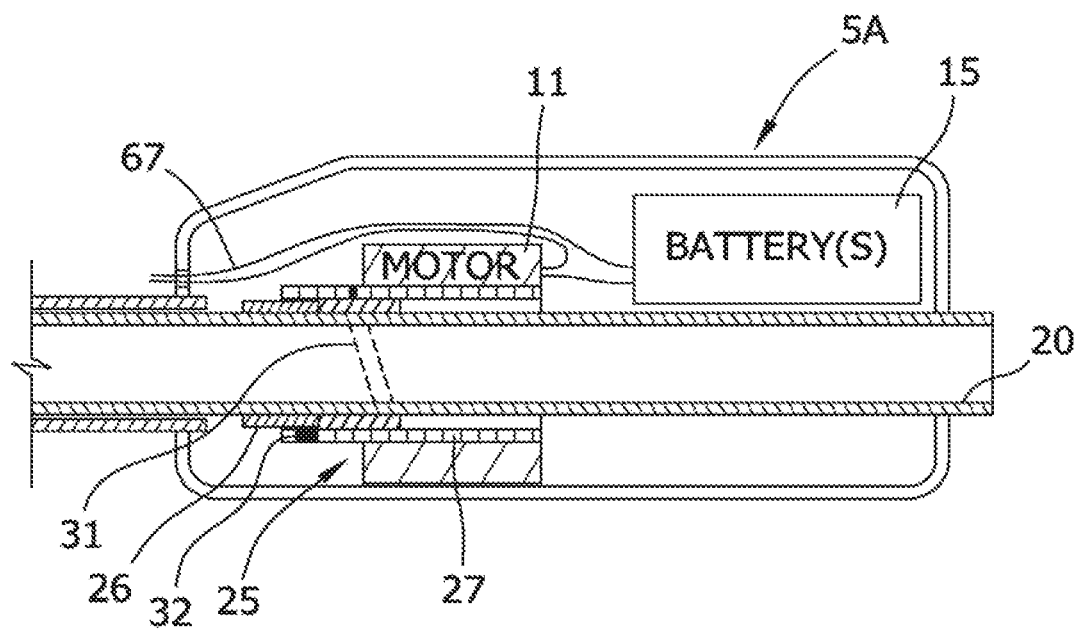
Figure 3:
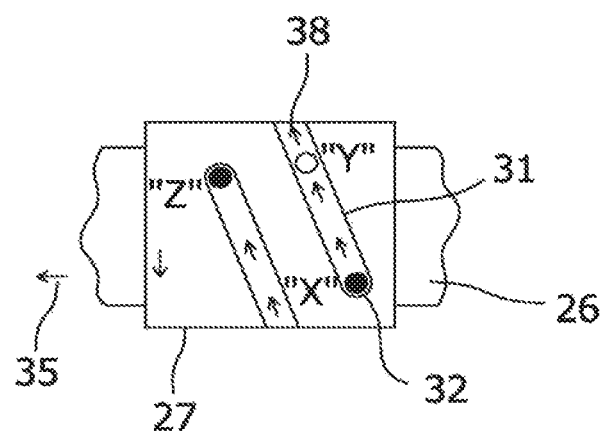
Figure 4:
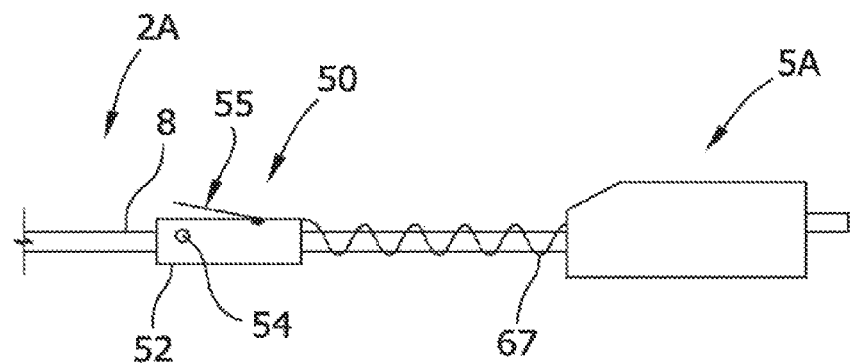
Figure 5A:
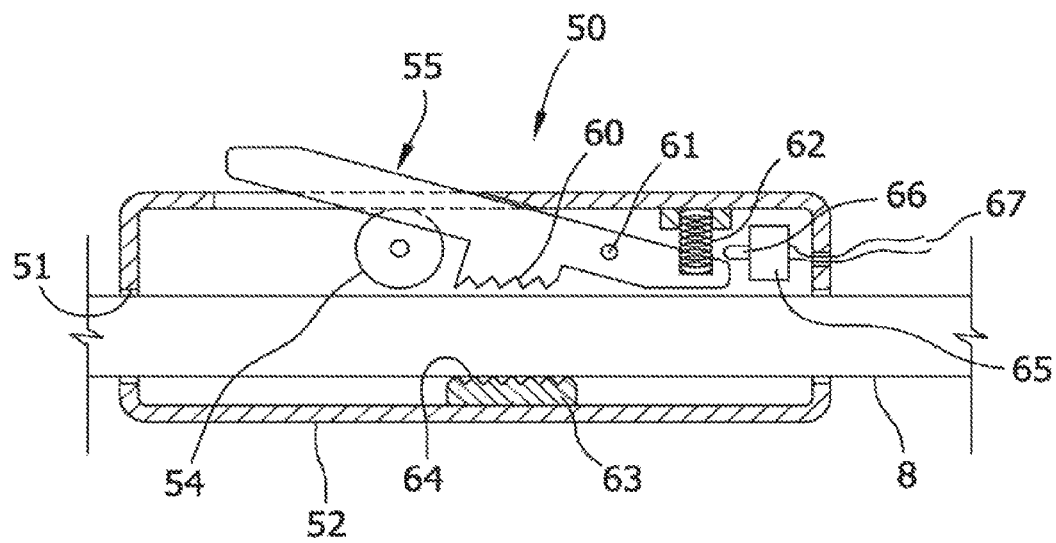
Figure 7A:
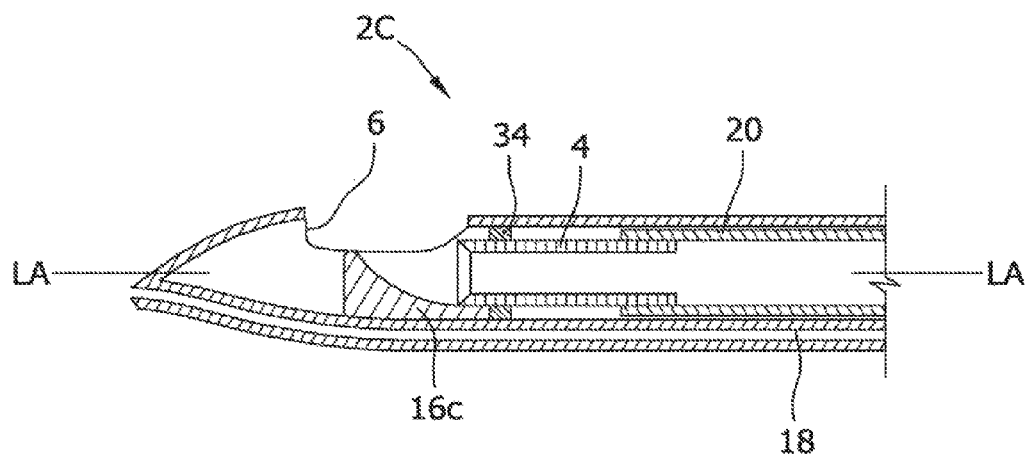
Figure 7B:
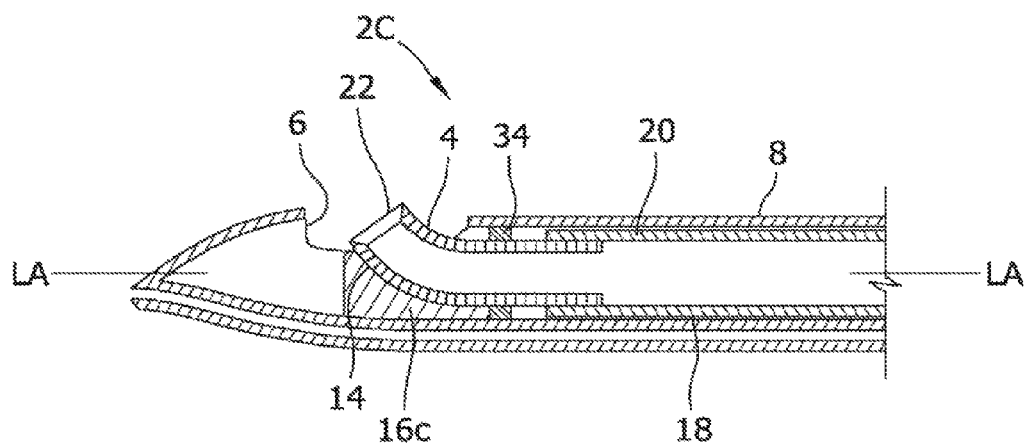
Figure 8:
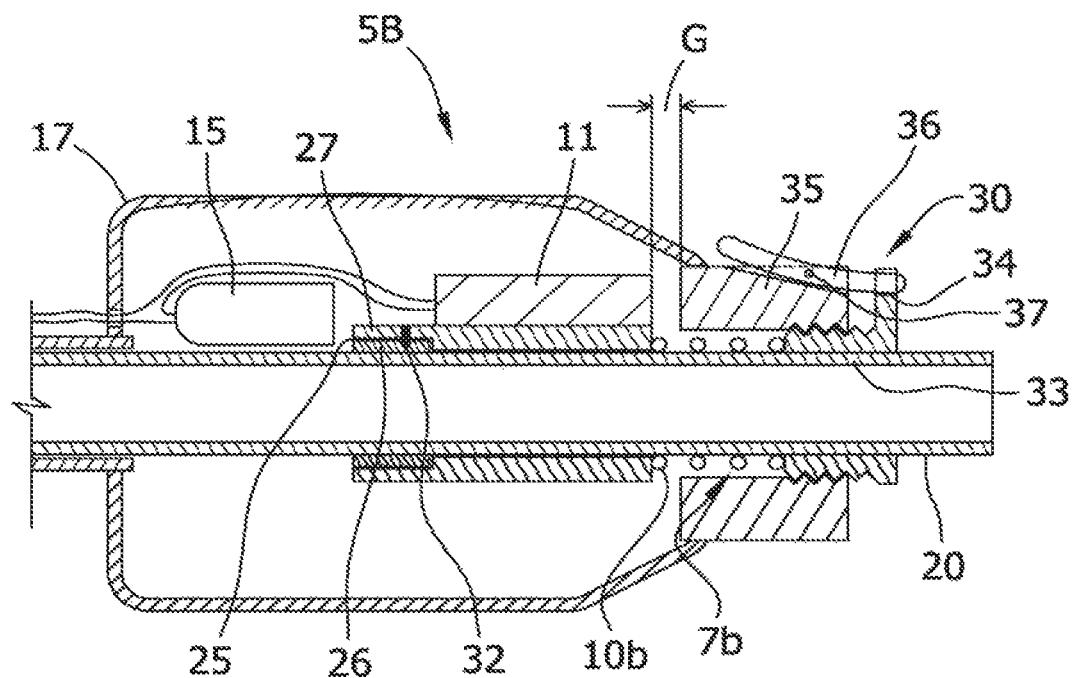
Figure 9:
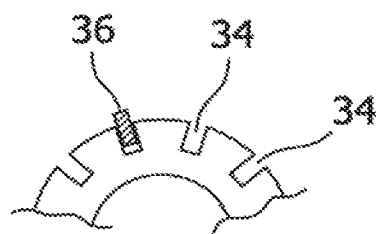
Figure 10A:
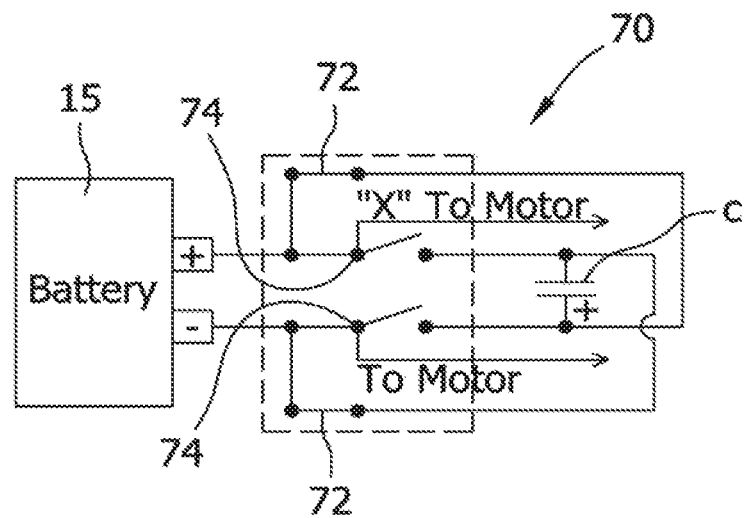
Figure 10B:
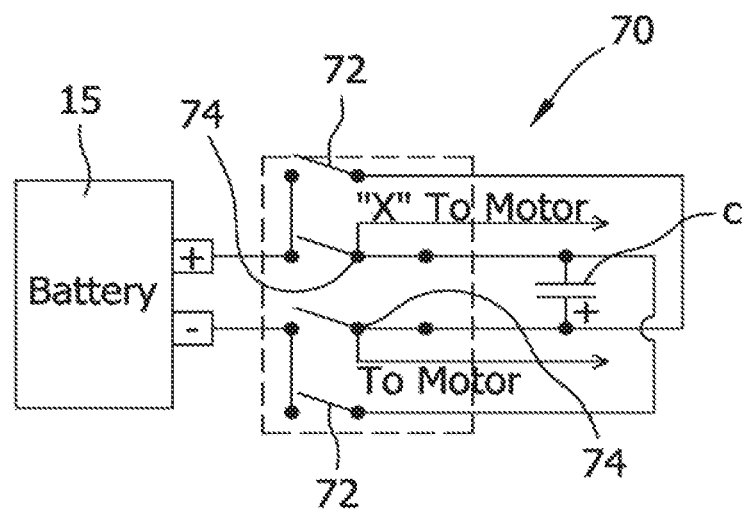
Figure 11A:
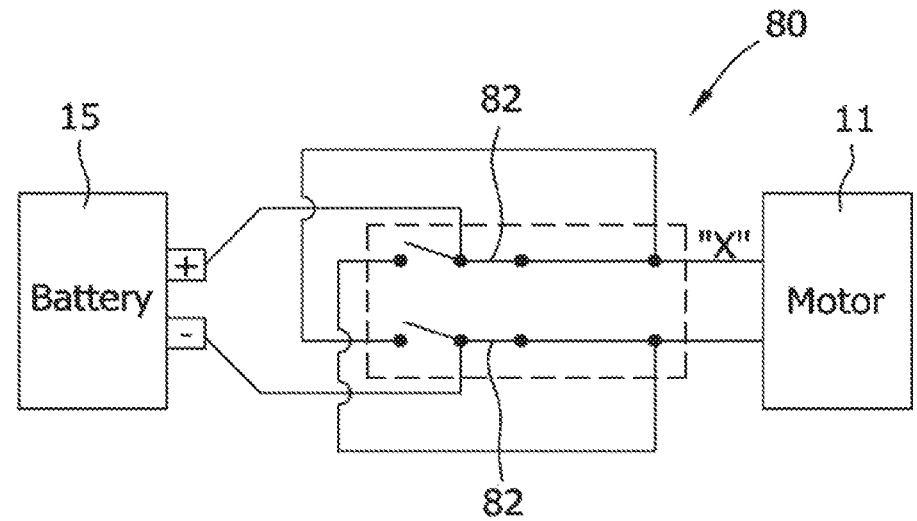
Figure 11B:
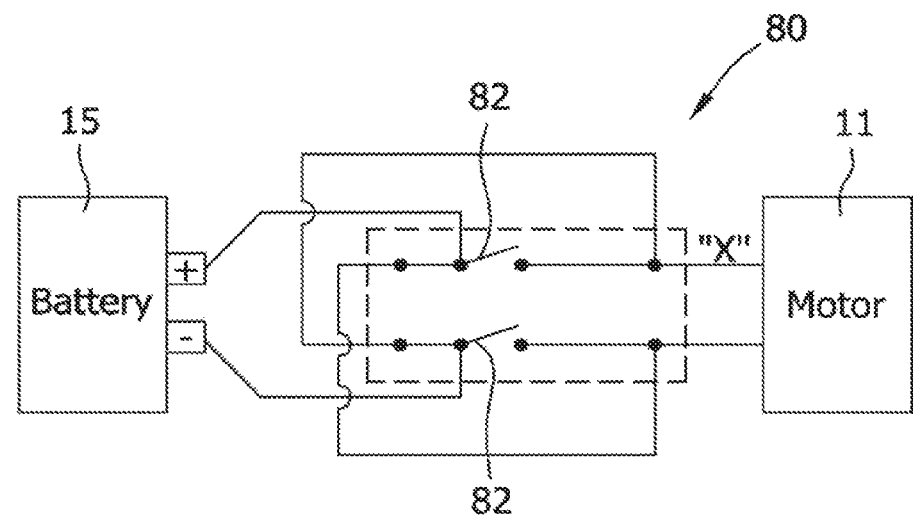

1A and 1C with an cam follower in a starting position relative to the cylindrical cam;

FIG. 2B is similar to FIG. 2A, except with the cam follower in an intermediate position relative to the cylindrical cam;

FIG. 3 is a schematic, fragmentary top view of the cam follower and the cylindrical cam;

FIG. 4 is a schematic of a side view of a controller and the cutter driver of FIG. 2A;

FIG. 5A is a schematic, longitudinal sectional view of the controller;

FIG. 5B is a schematic, cross-sectional view of the controller;

FIG. 6 is a schematic, fragmentary longitudinal sectional view of a distal end of a second embodiment of the atherectomy catheter;

FIG. 7A is a schematic, fragmentary longitudinal sectional view of a distal end of a third embodiment of the atherectomy catheter with a cutting element in a storage position;

FIG. 7B is similar to FIG. 7A, except with the cutting element in a cutting position;

FIG. 8 is a schematic longitudinal sectional view of a housing of a cutter driver of the atherectomy catheter of FIG. 7A with a cut depth adjuster;

FIG. 9 is a schematic, fragmentary end view of a proximal end of the cut depth adjuster;

FIG. 10A is a circuit diagram of a first embodiment of a driver circuit in a first configuration;

FIG. 10B is similar to FIG. 10A, except the driver circuit is in a second configuration;

FIG. 11A is a circuit diagram of a second embodiment of a driver circuit in a first configuration;

FIG. 11B is similar to FIG. 11A, except the driver circuit is in a second configuration.

DETAILED DESCRIPTION

Apparatus according to embodiments of the present invention will generally comprise catheters having catheter bodies adapted for intraluminal introduction to the target body lumen. The dimensions and other physical characteristics of the catheter bodies will vary significantly depending on the body lumen which is to be accessed. In the exemplary case of atherectomy catheters intended for intravascular introduction, the distal portions of the catheter bodies will typically be very flexible and suitable for introduction over a guidewire to a target site within the vasculature. In particular, catheters can be intended for "over-the-wire" introduction when a guidewire channel extends fully through the catheter body or for "rapid exchange" introduction where the guidewire channel extends only through a distal portion of the catheter body. In other cases, it may be possible to provide a fixed or integral coil tip or guidewire tip on the distal portion of the catheter or even dispense with the guidewire entirely. For convenience of illustration, guidewires will not be shown in all embodiments, but it should be appreciated that they can be incorporated into any of these embodiments.

Catheter bodies intended for intravascular introduction will typically have a length in the range from 50 cm to 200 cm and an outer diameter in the range from 1 French to 12 French (0.33 mm: 1 French), usually from 3 French to 9 French. In the case of coronary catheters, the length is typically in the range from 125 cm to 200 cm, the diameter is preferably below 8 French, more preferably below 7 French, and most preferably in the range from 2 French to 7 French. Catheter bodies will typically be comprised of an organic polymer which is fabricated by conventional extrusion techniques. Suitable polymers include polyvinylchloride, polyurethanes, polyesters, polytetrafluoroethylenes (PTFE), silicone rubbers, natural rubbers, and the like. Optionally, the catheter body may be reinforced with braid, helical wires, coils, axial filaments, or the like, in order to increase rotational strength, column strength, toughness, pushability, and the like. Suitable catheter bodies may be formed by extrusion, with one or more lumens being provided when desired. The catheter diameter can be modified by heat expansion and shrinkage using conventional techniques. The resulting catheters will thus be suitable for introduction to the vascular system, including both coronary arteries and peripheral arteries, by conventional techniques.

The side openings or cutting windows of the atherectomy catheters of embodiments of the present invention may have a length of approximately 2 to 6 mm. In other embodiments, however, the opening or cutting window can be larger or smaller, but should be large enough to allow the cutter to protrude a predetermined distance that is sufficient to cut or debulk material from the body lumen at a treatment site.

FIGS. 1 to 5B show various portions or features of an atherectomy catheter 2A. As shown in FIGS. 1A and 1B, the catheter 2A has a nosecone 3a, a tubular body 8 and a side opening 6. The catheter 2A also includes a flexible cutting element, generally indicated at 4, coupled to a flexible rotatable shaft 20, and is used to cut material from a blood flow lumen such as a blood vessel. Flexible cutting element 4 is coupled to the distal end of flexible rotatable shaft 20. Cutting element 4 may comprise a first tubular member and shaft 20 may comprise a second tubular member. The first tubular member has an outer diameter sized to be received within the inner diameter of the second tubular member so that an outer surface of the first tubular member may be bonded or otherwise fixed to the inner surface of the second tubular member. By manipulating shaft 20, cutting element 4 is movable between a stored position (FIG. 1A) and a cutting position (FIG. 1B). In the stored position, the axis of rotation of the cutting element 4 is parallel to the longitudinal axis LA of the tubular body 8 as seen in FIG. 1A. In the cutting position the axis of rotation of the cutting element 4 is deflected between the proximal and distal ends of the cutting element and at least a portion of a distal tip 19 of cutting element 4 extends through side opening 6 beyond an outer diameter of tubular body 8 as shown in FIG. 1B. Distal tip 19 may comprise a cutting edge 22. Distal tip 19 may also comprise abrasive material, teeth, fins or other similar structures (not shown) which fragment tissue or material without cutting. As the axis of rotation of the cutting element 4 is deflected from the longitudinal axis LA of the tubular body 8 towards side opening 6, a portion of the distal tip 19 extends outwardly from the tubular body 8 and through side opening 6 beyond an outer diameter of the tubular body.

As described above, flexible cutting element 4 and rotatable shaft 20 may be comprised of multiple parts or tubular members subsequently joined together by welding, soldering, brazing, adhesive bonding, mechanical interlock or other means. Alternatively, cutting element 4 and rotatable shaft 20 may be formed from one continuous part which may be a single tubular member having sufficient flexibility at its distal end portion.

Flexible cutting element 4 and rotatable shaft 20 may be made from any suitable material having sufficient flexibility, for example, braided wires, helically wound wires or a solid tube that may be spiral cut to give added flexibility. Flexible cutting element 4 and rotatable shaft 20 may be made from any suitable polymer or metal or combination thereof. Further, cutting element 4, rotatable shaft 20 or both, could be a solid tube made from a suitable metal or polymer that has been provided with spiral cuts to give the tube added flexibility.

Figure 1A:
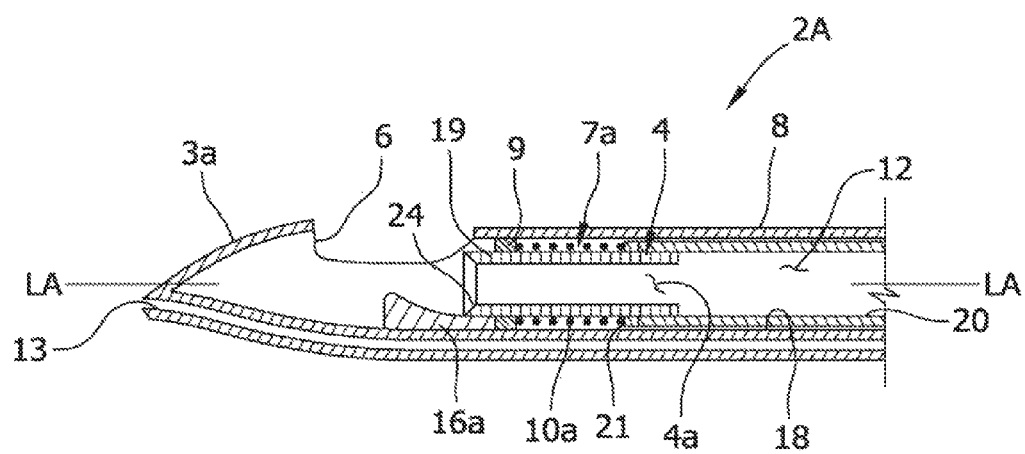
FIG. 1A is a schematic of a fragmentary, longitudinal sectional view of a distal end portion of an atherectomy catheter with a cutting element in a stored position.
Figure 1B:
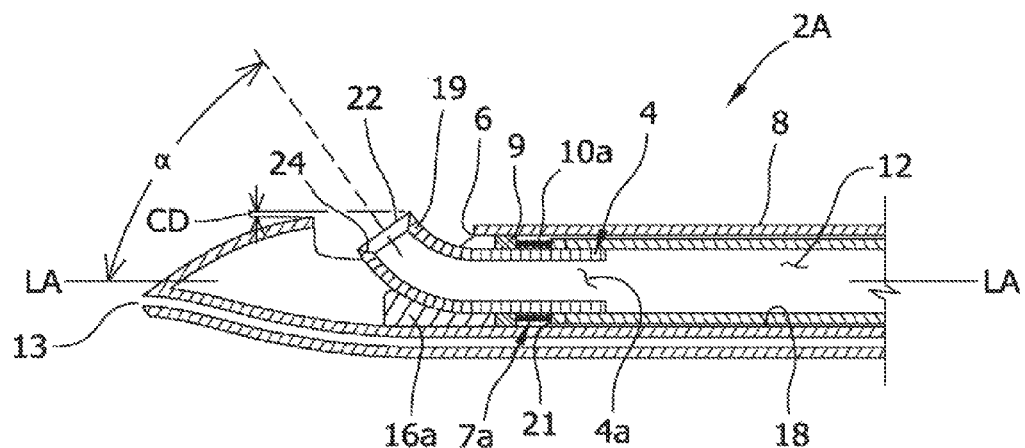
FIG. 1B is similar to FIG. 1A, except with the cutting element in a cutting position.
Figure 1C:
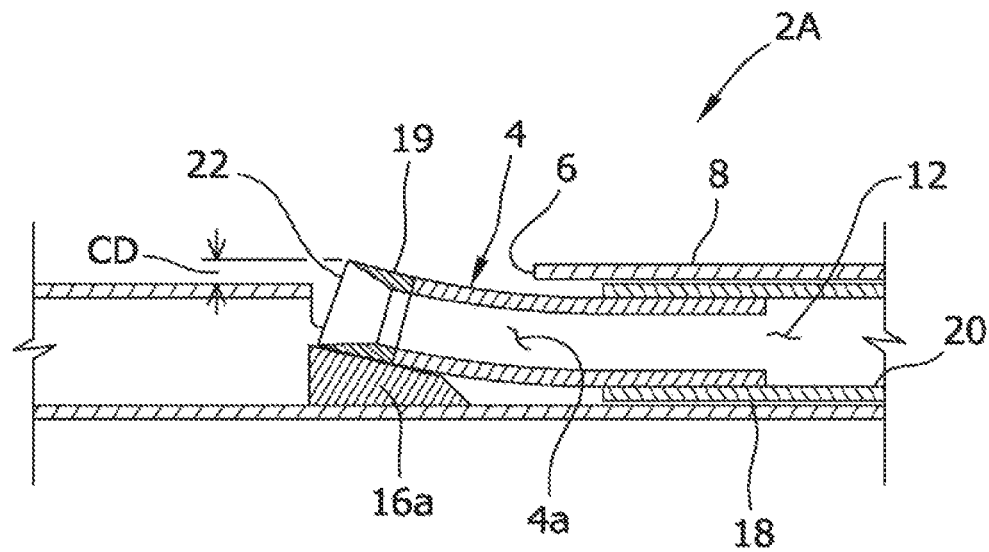
FIG. 1C is a schematic, fragmentary side cross-sectional view of a distal end portion of an alternative embodiment of the atherectomy catheter.

As shown in FIG. 1C, distal tip 19 may be a separate part or element made of a material different from material used in other portions of the cutting element 4. For example, distal tip 19 may be formed from a sufficiently hard material, such as tungsten carbide, that can be formed into and maintain the cutting edge 22 or other tissue fragmenting structure in a sharp condition. It should be noted that both the drive shaft 20 and cutting element 4 may be made from the same materials or different materials depending upon the application.

During use, a distal end of catheter 2A is positioned near a treatment site of a vessel with cutting element 4 in the stored position (FIG. 1A). Cutting element 4 is moved to the cutting position shown in FIG. 1B by advancing shaft 20 distally. Next, catheter 2A may be moved distally through the vessel with the cutting element 4 in the working or cutting position and simultaneously rotating about its central axis as described in further detail below. As catheter 2A moves through the blood vessel with the cutting edge 22 rotating in the working or cutting position, any tissue, cellular debris, plaque, blood or other material cut or fragmented by the cutting edge of cutting element 4 is directed into a hollow lumen 4a of cutting element 4, and into a tissue chamber 12 positioned proximal to the cutting element 4. Tissue chamber 12 may be the hollow luminal portion of rotatable shaft 20. In this design the catheter nosecone 3a need not be sized to accommodate the collection of tissue and can, therefore, be reduced in size or designed to house visualization equipment as described in connection with FIG. 6. Since the tissue collection chamber 12 is not constrained in size by the size of the nosecone 3a it can be made any desired size up to the length of the catheter body 8 proximal of the cutting element 4.

A vacuum source (not shown) may additionally be supplied at a proximal end of tubular body 8 and may further aid in the collection and transport of any material cut and collected at the treatment site. The vacuum source may suction debris at the treatment site into the hollow lumen 4a of the cutting element 4 and into tissue chamber 12 of rotatable shaft 20. Additionally, the vacuum source may be configured to suction debris at the treatment site, into the hollow lumen 4a of the cutting element 4, into the tissue collection chamber 12 and out through a proximal end of catheter 2A. The vacuum source can control the suction of material that is collected and transported through pinch valves or other control means depending upon the application. In this way, tissue chamber 12 is not limited by any storage or size constraints and could be any desired length of the catheter body 8.

To expose distal tip 19 of cutting element 4 through side opening 6, rotatable shaft 20 and the cutting element coupled thereto are moved distally from the stored position. As distal movement progresses, cutting element 4 rides along a ramp 16a attached to the tubular body 8. The interaction between the cutting element 4 and the ramp 16a deflects the cutting element 4 into the cutting position in which the axis of rotation is deflected between the proximal and distal ends of the cutting element and away from the longitudinal axis LA of the catheter. As seen in FIG. 1B, when the cutting element 4 is in the cutting position a proximal portion of the cutting element has an axis of rotation that is generally aligned with the longitudinal axis LA of the catheter 2A while a distal portion of the cutting element (including distal tip 19) has an axis of rotation that is deflected from the longitudinal axis LA of the catheter by an angle $\alpha$. Angle $\alpha$ is selected to be steep enough to expose the cutting edge 22 through the side opening 6 to a desired cutting depth CD without requiring the opening to be undesirably long. For example, the angle $\alpha$ may be in the range of 10° to 30°. The dimensions of cutting depth CD may vary depending upon the material to be cut, the vessel being treated and the application of the catheter 2A. As described in more detail hereafter, the cutting depth CD may be adjustable so the cutting depth may be controlled as desired depending on the application for which the catheter is used.

In some embodiments, catheter 2A may have a pre-shaped curvature of the distal portion of tubular body 8 that may assist in urging cutting element 4 into position against the vessel luminal surface such that distal advancement of the entire catheter body 8 can move the rotating cutter through the occlusive material of the luminal vessel. Because the cutting element 4 has a cutting depth CD that is a distance beyond the outer diameter of the tubular body 8 of the catheter outside the side opening 6, the user does not have to invaginate the tissue into the side opening. The pre-shaped urge of the catheter 2A also assists in the distal advancement of the catheter through the torturous anatomy of the luminal vessels.

The catheter 2A may be configured as an over the wire catheter or as a rapid exchange catheter also known as a monorail catheter. For example, as shown in FIGS. 1A and 1B, the tip of the catheter 2A can include a lumen 13 having a distal opening and a proximal opening that is sized to receive a guidewire, having a diameter of about 0.014 in., about 0.018 in., about 0.035 in. or any other suitable diameter.

With continued reference to FIGS. 1A and 1B, the catheter 2A may have biasing mechanism, generally indicated at 7a, coupled to the distal end of rotatable shaft 20, proximal to side opening 6. The biasing mechanism 7a is configured to bias the cutting element 4 toward the stored position. The biasing mechanism 7a may also aid in preventing cutting element 4 from extending out of side opening 6 more than a desired cutting depth CD. Biasing mechanism 7a may include a stop 9 such as a continuous or discontinuous ring or other suitable means and a retraction member 10a such as a spring (e.g., a compression spring) or other suitable resilient member. The stop 9 may be coupled to tubular shaft 8 at a location proximal of side opening 6. One end of retraction member 10a may be adjacent a proximal side of stop 9 and the other end may be adjacent to the distal end of rotatable shaft 20. The distal end of rotatable shaft 20 may optionally include a stop shoulder 21 to help reinforce the distal end of the rotatable shaft against the retraction member 10a. Retraction member 10a is in a resting or non-compressed condition when the cutting element 4 is in the stored position and is in a compressed condition when the cutting element is in the cutting position. When a force is applied to the rotatable shaft 20 to move cutting element 4 distally from the stored position to the cutting position, the rotatable shaft compresses (broadly, "deforms") retraction member 10a. Compression of the retraction member 10a creates a retraction force that is stored within the biasing mechanism. When the force compressing the resilient retraction member 10a is no longer applied, the retraction force stored by the compression of retraction member 10a pushes rotatable shaft 20 proximally to return cutting element 4 to the stored position.

As shown in FIG. 1B, the force supplied to distally move the rotatable shaft 20 and cutting element 4 from the stored position to the cutting position compresses retraction member 10a between the distal end of shaft 20 and stop 9 and creates a retraction force stored within the retraction member 10a. Stop shoulder 21 may reinforce the distal end of the rotatable shaft 20 to prevent wear from rotation of shaft 20 against retraction member 10a and/or any structural fatigue that may occur from the forces of the compression. The compression of retraction member 10a may continue until maximum compression of the retraction member occurs against the stop 9 producing a maximum cutting depth CD of cutting element 4 through side opening 6. It should be understood that maximum compression of the retraction member 10a is not necessary and that less than full compression of the retraction member may occur depending upon the application, thereby allowing variability in the cutting depth of the cutting element 4. When the force is no longer applied to rotatable shaft 20, the retraction force stored by the compression of retraction member 10a acts against stop 9 and pushes the distal end of rotatable shaft 20 in a proximal direction thus moving the cutting element 4 to the stored position.

Referring to FIGS. 1A and 1B, the cutting element 4 may have an inclined surface 24, which directs the tissue cut by the cutting edge 22 into the tissue chamber 12. Cutting edge 22 (and/or abrasive material, teeth, fins or other structure to fragment tissue) may be at a radially outer edge of the cutting element 4. In some embodiments the inclined surface 24 may be a smooth and continuous surface free of teeth, fins or other features, which disrupt the smooth nature of the surface. In other embodiments, the inclined surface 24 may have a limited amount of teeth, fins or other features that function to fragment and/or cut tissue.

As shown in FIGS. 2A and 2B, rotatable shaft 20 extends through a lumen 18 in catheter 2A to an exemplary cutter driver or handle 5A which is coupled to a proximal end of catheter 2A. Cutter driver 5A includes a motor 11, a power source 15 (for example one or more batteries), a microswitch (not shown), a housing 17, and a rotation assembly 25 for imparting translation and rotation to rotatable shaft 20 from motor 11. Cutter driver 5A can act as a handle for the user to manipulate catheter 2A. A lever, trigger, or other suitable actuation means (not shown), when actuated, closes the microswitch, electrically connecting power source 15 to motor 11, and thereby, rotating rotatable shaft 20 and cutting element 4. Cutting element 4 is rotated about 1 to 160,000 rpm but may be rotated at any other suitable speed depending upon the particular application.

In the illustrated embodiment, the rotation assembly 25 includes a cylindrical cam 27 connected to an output shaft (not shown) of the motor 11, and a cam follower 26 connected to the rotatable shaft 20, as shown in FIGS. 2A, 2B and 3. The cam follower 26 may be fixedly secured to the rotatable shaft 20 by welding, soldering, brazing, adhesive bonding, mechanical interlock or other means and may be made from metal such as steel, or other metals, or engineering polymer such as polyester, liquid crystal polymer, nylon, or other polymers. The cam follower 26 has a substantially cylindrically shaped body as shown in FIGS. 2A and 2B or may have other shapes. The cam follower 26 includes a projection 32 (e.g., a pin or roller) that extends outwardly from the body. Projection 32 may be a pin shaped member although other shapes are suitable. The cam follower 26 and the projection 32 may be separate parts which are suitably bonded or joined together or they may be a single integrated part. For example, projection 32 can be molded, welded, soldered, brazed, adhesive bonded, mechanical interlocked or other suitable means to cam follower 26.

As best seen in FIG. 3, the cylindrical cam 27 has a spiral slot 31 that accepts the projection 32 from the cam follower 26. In the illustrated embodiment, the spiral slot 31 extends through the wall of the cylindrical cam 27, although the spiral slot may instead be an internal groove on the interior surface of the cylindrical cam. The spiral slot 31 of cylindrical cam 27 may have a starting position X toward a proximal end of the cylindrical cam, and an extended position Z toward a distal end of the cylindrical cam wherein the direction of rotation may be counterclockwise as shown by arrows 38 in FIG. 3. It should be understood, however, that the position of the spiral slot 31 within the cylindrical cam 27 is not limiting and that the starting point may be located toward the distal end and the extended position may be located toward the proximal end of the cylindrical cam 27 depending upon the direction of rotation and the application. It should further be understood that the starting position X and extended position Z do not have to be located at the ends of the spiral slot 31 and both could be located at any desired location within the spiral slot. It should also be understood that the angle of the spiral slot 31 relative to the longitudinal axis of the cylindrical cam 27 can be varied to suit the design requirements of specific anatomies.

As rotation is supplied to cylindrical cam 27 from the motor 11, the cam follower 26 translates (i.e., moves linearly) as it follows the cylindrical cam within the slot 21, thereby imparting translation or linear movement of the shaft 20. In particular, the shaft 20 and the cutting element 4 move distally, as shown by arrow 35 in FIG. 3, from the stored position shown in FIG. 1A to the cutting position shown in FIG. 1B. As rotatable shaft 20 moves distally, a retraction force in the proximal direction is created by the compression of retraction member 10a. When the projection 32 of the cam follower 26 has completely advanced to the extended position Z of the spiral slot 31, the cam follower rotates with the cylindrical cam 27, thereby imparting rotational movement of the shaft 20. During rotation of the cam follower 26 and the shaft 20, distal movement of the cam follower, the shaft and the cutting element 4 is halted and compression is maintained to the retraction member 10a. The length of the spiral slot 31 from the starting position X to the extended position Z can determine the distance the cutting element 4 extends distally from the stored position to the cutting position. It should be understood that the distance that the projection 32 of the cam follower 26 travels within the spiral slot 31 of the cylindrical cam 27 is not limiting and that the spiral slot can be given various lengths corresponding to various cutting depths as desired.

When rotation of the cylindrical cam 27 by the motor 11 is halted, rotation of the cam follower 26 is also halted, as is that of the rotatable shaft 20 and the cutting element 4. Additionally, when the rotational force is halted, the retraction force stored by the compression of retraction member 10a acts against the rotatable shaft 20 and pushes/retracts the rotatable shaft 20 proximally from the cutting position to the stored position. Projection 32 of cam follower 26 also retracts within the spiral slot 31 of cylindrical cam 27 from the extended position Z toward the starting position X.

It should be further understood that if the retraction member 10a reaches maximum compression before the projection 32 reaches the extended position of the spiral slot 31, distal movement of the rotatable shaft 20 may be halted while rotation of the cam follower 26 and the cylindrical cam 27 is maintained. Therefore, the compression length of the retraction member 10a and, depending upon the application, the compression length of the retraction member against the stop, may also be utilized to control the cutting depth of the catheter 2A. It should be still further understood that in some applications the retraction member 10a may not be utilized and battery power, counter rotation of the motor or alternate means may be used to return the cutting element 4 from the cutting position to the stored position.

FIGS. 4, 5A and 5B illustrate an optional controller 50 that may be rotatably and/or slidably coupled to tubular body 8 and may be configured for one-handed use by an operator of the catheter 2A. Controller 50 is tethered to handle 5A by wires 67 as will be described in more detail hereafter. Controller 50 functions as an optional secondary controller which allows an operator to activate motor 11 and/or grasp the torque shaft or tubular body 8 at a location remote from handle 5A which is proximate or at least closer to the catheter access site in the patient's body. Controller 50 comprises a body 52 that may have left and right housing halves, a lumen 51 that accepts the torque shaft or tubular body 8, a button 54 and a lever, generally indicated at 55. A portion of lever 55 extends from body 52 through an opening in the body. Button 54 includes a button compression member 56 (FIG. 5B) such as a spring or the like and is housed at one end in receiving cavity 57 of button 54. The other end of button compression member 56 is received in a pocket 58 of body 52. Button 54 further includes a slot 59 that accepts the lever 55 when the slot is aligned with the lever as described in more detail hereafter. Button 54 has an extended or at rest position and a depressed position. Button compression member 56 keeps the button 54 in the extended or at rest position until the button 54 is depressed by an operator.

Referring to FIG. 5A, the lever 55 includes teeth 60, a pivot pin 61 and a lever compression member 62. When the lever 55 is depressed, the tubular body 8 is sandwiched or compressed between the teeth 60 of the lever and an anvil 63 having teeth 64. In the illustrated embodiment, the teeth 60, 64 are broadly, "body engaging elements." Controller 50 also includes an activator switch 65 having an activator button 66 in electrical communication with the control wires 67. Control wires 67 electrically connect the activator switch 65 to the battery 15 and the motor 11 of cutter driver 5A. Body 52, lever 55, anvil 63, teeth 60 and 64 and buttons 54 may be made from polycarbonate, nylon, or other materials and may be injection molded or otherwise fabricated into the desired configuration. The lever 55, button compression member 56, pivot pin 61, anvil and teeth 60 and 64 may also be comprised of metal such as steel, spring steel, or other metals, or engineering polymer such as polyester, liquid crystal polymer, nylon, or other polymers. Body 52 may be molded in two halves and the halves bonded together by ultrasound, snap fit, adhesives, or other means.

Lever 55 is configured such that it can be depressed a first amount to a first position when button 54 is in the extended or at rest position and to a second position when button is depressed. When lever 55 is depressed to the first position teeth 60 move toward teeth 64 resulting in shaft 8 being gripped between teeth 60 and 64. Controller 50 can thus be used to manipulate shaft 8 rotationally and axially when lever 55 is in the first position. Movement of the lever 55 to the second position supplies power to the motor 11 to extend and rotate the cutting element 4. However, lever 55 cannot be moved from the first position to the second position unless button 54 is depressed by the operator. This prevents the operator from inadvertently or accidentally engaging the motor 11 before the operator is ready to begin the tissue cutting or fragmenting procedure. During use, when the operator desires to begin the cutting operation button 54 is depressed to move slot 59 to a position which aligns with lever 55. In this aligned position, the exposed portion of lever 55 may be depressed which causes a portion of lever 55 to be received into slot 59. Depression of the lever 55 causes the lever to pivot about pin 61 so that a portion of lever 55 also contacts and depresses activator button 66 of activator switch 65. The activator switch 65 is in communication with the battery 15 and the motor 11 of the cutter driver 5A through the control wires 67, thereby electrically connecting the power source to the motor to thereby engage and rotate the rotatable shaft 20 and, depending upon the application, cause distal movement of the rotatable shaft and cutting element 4 to the cutting or working position.

In use controller 50 is positioned at the desired location along the torque shaft or tubular body 8 that is to be mechanically manipulated (advanced, retracted, torqued). The user depresses lever 55 to the first position causing teeth 60 and 64 to grip the tubular body 8 and allow the mechanical manipulation of the catheter body 8. When the catheter has been positioned at a desired location the operator depresses button 54 which allows lever 55 to be depressed to the second position. The depression of lever 55 to the second position engages activator button 66 that is in electrical communication with the motor 11 of the cutter driver 5A by control wires 67, activating remote manipulation of the rotation and distal movement of the rotatable shaft 20 and cutting element 4 with the controller 50.

FIG. 6 illustrates an alternate catheter embodiment indicated generally at reference numeral 2B. Catheter 2B is substantially similar to catheter 2A of FIGS. 1 to 5 except that it is provided with imaging capabilities. Catheter 2B has an extended nosecone 3b that houses and protects a transducer 40 having vessel imaging capabilities, located distal to cutting element 4. Transducer 40 may be connected to a non-catheter based control using one or more of wires, cables, connectors, wireless communication, or other means. Signal processing or signal conditioning components, either catheter based or non-catheter based, may be interspersed between the transducer and the control, or may be integrated on the transducer, the controller or any combination thereof. Imaging transducers are catheter based and may transduce ultrasonic energy, light energy, infrared energy, magnetic energy, X-ray energy, or combinations thereof. Some examples of known imaging modalities suitable for use in catheters disclosed herein include intravascular ultrasound (IVUS), optical coherence tomography (OCT), and magnetic resonance imaging (MRI). While the remaining discussion is directed at IVUS, it will be appreciated that the catheters, systems and methods of the embodiments described herein can be comprised of any of IVUS, OCT or MRI imaging.

Transducer 40 may be fragile and prone to breaking and kinking as the catheter is advanced in the vessel or lumen. Nosecone 3b may protect transducer 40 by carrying or translating the mechanical stresses and forces surrounding transducer 40. The outer wall of nosecone 3b may comprise material having a thickness or having properties that minimizes acoustic attenuation by allowing better penetration of the acoustic ultrasound signal produced by the transducer through the outer wall of the nosecone, thus improving the quality of imaging. In order to better preserve the structural integrity of the outer wall of the nosecone 3b, structural support ribs (not shown) may be provided. Outer wall of nosecone 3b may be provided with one or more optional slot(s) 41 that are axially aligned with transducer crystals of transducer 40 allowing acoustic ultrasonic sound pulses to travel between transducer crystals and the vessel wall in such a way as to minimize attenuation or interference. Although transducer 40 will produce a 360° image of the vessel through the outer wall of nosecone 3b and the optional slot 41, the radial angled portion of the 360° imaged vessel obtained through the slot may be of a higher quality than the remainder of the radial angled portion of the 360° imaged vessel obtained through the outer wall of nosecone. Thus a larger dimensioned slot 41 may be preferred, particularly in the direction that cutter 4 protrudes through window. Slot 41 may produce a radial angle of the imaged vessel in the range of 60° to 180° of the circumference of the vessel. To minimize any effect of distortion and to minimize the amount or size of any artifacts in the image, the edges of the opening of slot 41 may be shaped or angled to coincide with the radius of the catheter 4.

Slot 41 may be positioned directly distal of the side opening 6 so the physician is able to view with greater clarity and accuracy what will be cut or removed at a treatment site in a vessel or lumen as the catheter is advanced distally in the lumen with the cutting element 4 in the cutting position. Additionally, after the material has been cut the catheter 2B can be retracted proximally in the vessel lumen until slot 41 is adjacently aligned with the treatment site so that the physician is able to view with greater clarity and accuracy what has been cut or removed from the treatment site.

Catheter 2B has further been provided with an extended ramp surface 16b that extends from side opening 6 to the inside luminal surface of tubular body 8 opposite the side opening. It should be understood that the ramp surface 16b is not limiting and that the size, slope, width and length of the ramp surface could be any dimension or angle as desired depending upon the application.

FIGS. 7A, 7B, 8 and 9, show an alternative catheter embodiment, catheter 2C, that includes an alternative biasing mechanism and a cut depth adjustment controller. Catheter 2C has properties and features similar to catheter 2A except as described below. FIG. 7A illustrates a partial side cross-sectional view of a distal end of catheter 2C with a flexible cutting element, generally indicated at 4, in a storage position. FIG. 7B illustrates the partial side cross-sectional view of the distal end of catheter 2C with the cutting element 4 in a cutting position. Catheter 2C is substantially similar to catheter 2A and includes tubular body 8 and side opening 6. The flexible cutting element 4 is coupled to the distal end of flexible rotatable shaft 20. By manipulating shaft 20 cutting element 4 is movable between a stored position (FIG. 7A) and a cutting position (FIG. 7B). In the stored position the axis of rotation of the cutting element 4 is parallel to the longitudinal axis LA of the tubular body as seen in FIG. 7A. In the cutting position the axis of rotation of the cutting element 4 is deflected between the proximal and distal ends of the cutting element and at least a portion of a cutting edge 22 of cutting element extends through side opening 6 beyond an outer diameter of tubular body 8 as shown in FIG. 7B. A portion of the cutting edge 22 extends outwardly from the tubular body 8 and through side opening 6 beyond an outer diameter of the tubular body when the cutting element 4 is deflected.

To expose cutting edge 22 of cutting element 4 through side opening 6, rotatable shaft 20 and the cutting element coupled thereto are moved distally from the stored position to the cutting position. As distal movement progresses cutting element 4 rides along the ramp 16c coupled to the tubular body 8 of catheter 2C. The interaction between the cutting element 4 and the ramp 16c deflects the cutting element 4 into the cutting position in which the axis of rotation of the cutting element is deflected between the proximal and distal ends of catheter 2C and away from the longitudinal axis LA of the catheter. At least a portion of the cutting edge 22 extends through side opening 6 beyond an outer diameter of tubular body 8 and toward the tissue to be cut at a treatment site. Catheter 2C may have optional stop 34 such as a continuous or discontinuous ring or other suitable means positioned proximal to side opening 6. Stop 34 is positioned to engage a distal end of shaft 20 and prevent further distal movement of the shaft. Stop 34 may aid in preventing over extension of the cutting element 4 through side window 6. Stop 34 also serves as a bushing for the cutting element 4, eliminating an excessive annular gap between the cutting element and the body 8 and preventing wear of the body 8 due to contact with the cutting element 4 as the cutting element rotates.

As shown in FIG. 8, rotatable shaft 20 extends through lumen 18 in catheter 2C to cutter driver 5B. Cutter driver 5B includes a motor 11, a power source 15 (for example one or more batteries), a microswitch (not shown), a housing 17, and a rotation assembly 25, including a cam follower 26 and a cylindrical cam 27, for imparting translation and rotation to a rotatable shaft 20 from the motor 11. Each of these components is similar or identical to the corresponding components described above with respect to the catheter 2A, and therefore, the description set forth with respect to the catheter 2A applies to the present catheter 2C.

Catheter 2C includes an alternative biasing mechanism, generally indicated at 7b. Whereas the biasing mechanism 7a of catheter 2A was positioned at a distal location in the catheter body 8, the biasing mechanism 7b of catheter 2C is positioned generally within the handle 5B. Biasing mechanism 7b may include a stop 33 fixedly secured to the shaft 20, and a retraction member 10b such as a spring or other suitable means. One end of the retraction member 10b may be adjacent to a distal side of the stop 33 and the other end may be adjacent to the proximal end of the cylindrical cam 27 or other alternative fixed surface.

When rotation is supplied to cylindrical cam 27, the projection 32 of the cam follower 26 follows the cam within spiral slot 31. Rotation of the cylindrical cam 27 imparts translation (i.e., distal movement) of the rotatable shaft 20, the cutting element 4, and the stop 33, which compresses the retraction member 10b. The compression of retraction member 10b creates a retraction force stored within the compressed retraction member. When the projection 32 advances distally to the extended position, distal movement of shaft 20 is halted and the cam follower 26 rotates with the cylindrical cam 27, thus rotating the rotatable shaft 20 and the cutting element 4 and supplying continued compression to the retraction member 10b. When the rotational force to the cylindrical cam 27 is halted, rotation of the cam follower 26 and the rotatable shaft 20 is halted and compression is no longer supplied to the retraction member 10b. The cessation of compression to retraction member 10b releases the stored retraction force of the retracting member and proximally retracts projection 32 of the cam follower 26 toward the starting position of spiral slot 31 of cylindrical cam 27, thereby proximally retracting the rotatable shaft 20 and the cutting element 4 from the cutting position (FIG. 7B) to the stored position (FIG. 7A) parallel to the longitudinal axis LA.

It should be further understood that distal movement of the rotatable shaft 20 may be halted before the projection 32 of the cam follower 26 advances completely in the spiral slot 31 of the cylindrical cam 27 to the extended position if the retraction member 10b reaches maximum compression before the projection reaches the extended position of the spiral slot. Therefore, the compression length of the retraction member 10b and, depending upon the application, the compression length of the retraction member against the stop 33, may also be utilized to control the cutting depth CD of the cutting element 4.

As can be seen in FIGS. 8 and 9, the catheter 2C includes a cut depth controller, generally indicated at 30. The cut depth controller 30 comprises a threaded cut depth adjustment member 35 having one end rotatably coupled to the handle housing 17, such as by a slip-fit, and an opposite end threadably coupled to the stop 33. An adjustment lever 36 is coupled to the depth adjustment member 35 by a pivot pin 37. The adjustment lever 36 is receivable in one of a plurality of circumferential slots 34 in the stop 33. As described further below, the cut depth CD may be adjusted by rotating the adjustment 35 clockwise or counterclockwise to move the adjustment member proximally or distally with respect to the cylindrical cam 27.

In some embodiments of catheter 2C, the cut depth controller 30 controls the cutting depth CD of the cutting element 4 through the distal side opening 6 of tubular body 8. In particular, the adjustment member threaded on the stop 33 (and therefore, threaded on the rotatable shaft) is used to adjust the amount of translation of the shaft 20 before rotation is imparted to shaft via the cylindrical cam 27. A proximal end portion of the lever 36 is biased in a direction toward the slots 34 in the stop 33. A distal end portion of lever 36 may be depressed to pivot the proximal end portion of lever 36 away from slots 34. When the lever 36 is depressed, the adjustment member 35 may be rotated either clockwise or counterclockwise relative to the housing 17 and the stop 33 to move adjustment member toward or away from the cylindrical cam 27. Rotation of the adjustment member 35 the lever 36 with one of the slots 34. Each of the slots 34 corresponds to a different cut depth CD, and indicia (not shown) may be provided on the stop to indicate the relative cut depths associated with each slot. When the adjustment member 35 has been threaded on the stop 33 to a position where the lever 36 aligns with one of the slots 34 at a desired cut depth, the lever is released so that the proximal end portion of lever is received in the desired slot corresponding to a desired cutting depth CD. The lever 36 locks the cut depth adjustment member 35 into place when the lever is received in desired slot 34 to prevent any tightening or loosening of the cut depth adjustment member on the nut 33 during rotation and distal advancement of rotatable shaft 20.

In the present embodiment, the stop 33, coupled to the rotatable shaft 20, and the adjustment member 35 move distally toward the cylindrical cam 27 as the rotatable shaft 20 distally advances, due to rotation of the cylindrical cam. These components advance distally until the adjustment member 35 engages the cylindrical cam 27 (or other stop), whereby the shaft 20 can no longer advance distally. Upon engagement of the adjustment member 35 with the cylindrical cam 27 (or other stop), rotation of the cylindrical cam imparts rotation, rather than translation, to the cam follower 26 and the shaft 20. Accordingly, a length of a gap G between the adjustment member 35 and the cylindrical cam 27 (or other stop) determines (i.e., relates directly to) the cut depth CD of the cutting element 4. The length of the gap G is controlled by the cut depth controller 30. In particular, the distance that the cut depth adjustment member 35 is threadably coupled onto the stop 33 and locked into place by the accepting of lever 36 into one of slots 34, determines the length of the gap G between the cylindrical cam 27 (or other stop), and the adjustment member 35. The longer the length of the gap G, the longer the length that the projection 32 of the cam follower 26 can advance within the spiral slot 31 of the cylindrical cam 27 before the adjustment member 35 engages the cylindrical cam (or other stop) and the longer the length the cutting element 4 will distally move, thus the longer the length of the cutting depth CD of the cutting element 4. Alternatively, the less the cut depth adjustment member 35 is threadably coupled onto nut 33 and locked into place by the accepting of lever 36 into one of slots 34, the shorter the distance gap G is between the cylindrical cam 27 and the adjustment member. Thus, a smaller gap G results in a smaller cutting depth CD.

When rotation is no longer supplied to the cylindrical cam 27, and thereby, the rotatable shaft 20, the retraction force stored by the compression of the retraction member 10b pushes/retracts the rotatable shaft 20 to the stored position, thereby retracting the cutting element 4 from the cutting position down the ramp 16c and back to the stored position parallel to the longitudinal axis LA of the tubular body 8 of the catheter. It should be understood that in some embodiments the retraction member (10a, 10b) may be omitted. In some embodiments, the cutting element 4 may not be biased toward the stored position. For these applications, battery power or alternate means may be used to return the cutting element 4 from the cutting position to the stored position and is discussed in greater depth below.

During use of the catheter, the catheter 2A, 2B, 2C or any similar embodiment with features of catheter 2A to 2C, is advanced through the vessel with the cutting element 4 in the stored position until side opening 6 is positioned adjacent or just proximal to a proximal end of a treatment site of a vessel. The illustrated controller 50 may aid in the placement of the catheter 2A-2C adjacent or proximal the treatment site through the torturous anatomy of the vessels through mechanical manipulation (advancing, retracting, torquing). Cutting element 4 coupled to the rotatable shaft 20 is then moved distally from the stored position to the cutting position. Controller 50 may effectuate power to the motor 11 in order to advance the cutting element 4 to the cutting position. Alternatively, a trigger on cutter driver 5 may be used to effectuate power to the motor 11. Once the cutting element 4 has been distally advanced within the catheter body 8 and deflected outwardly through the side opening 6 of the tubular body 8 of the catheter to a desired cutting depth CD so that at least a portion of the cutting edge 22 (or teeth, fins, or other tissue fragmenting structure) of the cutting element extends beyond the outer diameter of the tubular body 8 of catheter, the catheter is pushed distally through the vessel with the cutting element 4 in the cutting position. As the catheter 2A-2C moves through the blood vessel, with the cutting element 4 in the working or cutting position, the tissue material is cut by the cutting edge 22 of cutting element 4 (or is fragmented by teeth, fins or other tissue fragmenting structure of the distal tip portion of the cutting element) and is directed into the tissue collection chamber 12 (e.g., a lumen of the rotatable shaft 20) positioned proximal to the cutting element. The tissue collection chamber 12 may extend the length of the catheter body 8.

In this embodiment and in the other catheter embodiments described herein, a vacuum source (not shown) may be applied at the proximal end of the catheter body 8 to aid in collection and transport of material cut by the cutting element 4 through rotatable shaft 20. As mentioned previously, any of the catheter bodies 8 described herein may be provided with a side wall opening or other opening at a proximal location which can be connected by tubing to a suction source so that debris created by the rotating cutter element 4 can be aspirated through the annular space between the catheter body and flexible rotatable shaft 20. The tissue collection chamber 12 may be as long as the catheter length which is proximal to the window. When the tissue material has been properly and effectively treated at the treatment site by the cutting element 4, power is halted to the motor 11 and the retraction member 10a, 10b retracts the cutting element back to the stored position and the catheter is retracted from the vessel.

FIGS. 10A and 10B are circuit diagrams of a drive circuit, generally indicated at 70, that drives motor 11 in a forward direction using power from the battery 15 during use of the catheter and subsequently drives the motor in a backward direction using capacitor power when battery power to the motor is switched off. This drive circuit 70 may be used in combination with the embodiments of catheters 2A to 2C and may also be used in embodiments of the catheter that do not utilize a biasing mechanism 7a, 7b for retraction of the cutting element 4. Thus, capacitor power can be used for retraction of the cutting element 4 solely or in addition to the biasing mechanism 7a, 7b.

The drive circuit 70 includes four switches: two single pole single throw (SPST) switches 72 and two single pole double throw (SPDT) switches 74. FIG. 10A shows the switches 72, 74 as they would be set when the catheter 2A-2C is used to cut material from a vessel lumen. The SPST switches 72 are in a closed position, and the SPDT switches 74 are closed on the left side relative to the central common pole and open on the right side, such that motor lead "X" and a positive lead of a capacitor C is connected to the positive terminal of the battery 15 and both the motor 11 and the capacitor are also connected to the negative terminal of the battery. FIG. 10B shows the switches 72, 74 as they would be set when power to the motor 11 is turned off. In FIG. 10B, the two SPST switches 72 are open and the two SPDT 74 switches are in an open position on the left side and in a closed position on the right side. In this configuration the battery 15 is disconnected from both the motor 11 and the capacitor C, the capacitor is connected to the motor, and motor lead "X" is connected to the negative terminal of the capacitor. Thus, the capacitor C will power the motor 11 in the opposite rotational sense as the circuit of FIG. 10A, until the capacitor's charge is discharged to the point where it can no longer turn the motor.

FIGS. 11A & 11B are circuit diagrams of a second embodiment of a drive circuit, generally indicated at 80, that will drive the motor 11 in a forward direction using power from the battery 15 and will subsequently drive the motor in a backwards direction using the battery power. This circuit 80 may be used in combination with the embodiments of catheters 2A to 2C and may also be used in embodiments of the catheter that do not utilize the biasing mechanism for retraction of the cutting element. Thus, battery power can be used for retraction of the cutting element 4 solely or in addition to the biasing mechanism 7a, 7b.

FIGS. 11A and 11B show two SPDT switches 82 connecting the battery 15 to the motor 11. In FIG. 11A both switches 82 are in a closed position on the right side relative to the central common pole such that motor lead "X" is connected to the positive terminal of the battery 15 and the motor 11 is also connected to the negative terminal of the battery. In FIG. 11B the two SPDT switches 82 are in an open position on the right side and in a closed position on the left side. In this configuration motor lead "X" is connected to the negative terminal of the battery 15. Thus, in the circuit configuration of FIG. 11B, the battery 15 will power the motor 11 in the opposite rotational sense as the circuit configuration of FIG. 11A. When the motor 11 is energized, such as by depressing controller lever 55 of the embodiment described with respect to FIG. 4, the motor is be activated by means of the circuit configuration shown in FIG. 11A to advance the cutting element 4 out of the side opening 6. When the controller lever 55 is allowed to spring back or rebound from the un-depressed position, the motor 11 is briefly activated by means of the circuit configuration shown in FIG. 11B to retract the cutting element 4 through the side opening 6 and into the body 8.

The above description and the drawings are provided for the purpose of describing embodiments of the invention and are not intended to limit the scope of the invention in any way. It will be apparent to those skilled in the art that various modifications and variations can be made without departing from the spirit or scope of the invention. Thus, it is intended that the present invention cover the modifications and variations of this invention provided they come within the scope of the appended claims and their equivalents. Further, while choices for materials and configurations may have been described above with respect to certain embodiments, one of ordinary skill in the art will understand that the materials and configurations described are applicable across the embodiments.

What is claimed is:

1. A catheter for removing material from a body lumen comprising:
    a tubular body having proximal and distal ends, a longitudinal axis, a side opening adjacent the distal end of the tubular body, and a lumen extending along the longitudinal axis of the tubular body;
    a rotatable shaft disposed within the lumen of the tubular body and having proximal and distal ends and a longitudinal axis extending between its proximal and distal ends;
    a ramp coupled to the tubular body adjacent the distal end of the tubular body and having an angular surface generally opposite the side opening;
    a flexible cutting element having proximal and distal ends, a longitudinal axis extending between its proximal and distal ends, and an axis of rotation extending between its proximal and distal ends, the proximal end of the cutting element being coupled to the rotatable shaft for imparting rotation of the cutting element about its axis of rotation, and the distal end of the cutting element having a cutting edge adapted to cut material from the body lumen; and
    a stop secured to the tubular body,
    wherein the cutting element and the rotatable shaft are longitudinally moveable within the tubular body between a stored position, in which the cutting element is received in the tubular body, and a cutting position, in which the cutting element engages the angular surface of the ramp and is deflected along its longitudinal axis such that at least a portion of the longitudinal axis of the cutting element is not parallel to the longitudinal axis of the tubular body and only a portion of the cutting edge extends through the side opening,
    wherein the cutting edge faces distally when the cutting element is in the cutting position such that the cutting element is configured to remove material from the body lumen as the cutting element rotates and the catheter is moved distally in the body lumen during use,
    wherein the stop inhibits the cutting edge from the extending completely outside the side opening when the cutting element is in the cutting position so that only a portion of the cutting edge extends through the side opening when the cutting element is in the cutting position.

2. The catheter of claim 1, wherein the flexible cutting element has a lumen extending longitudinally through the proximal and distal ends of the cutting element for receiving material cut by the distal end of the cutting element.

3. The catheter of claim 2, wherein the rotatable shaft has a lumen extending longitudinally in the shaft and in communication with the lumen of the cutting element for receiving cut material from the lumen of the cutting element.

4. The catheter of claim 1, further comprising a spring configured to bias the cutting element toward the stored position.

5. The catheter of claim 4, wherein the spring engages the stop to bias the cutting element toward the stored position.

6. The catheter of claim 5, wherein the spring is adapted to resiliently compress between the stop and the distal end of the rotatable shaft as the shaft and the cutting element are moved longitudinally within the tubular body to impart a retraction force on the shaft.

7. The catheter of claim 1, further comprising a nosecone distal to the side opening, and an imaging transducer housed within the nosecone.

8. The catheter of claim 7, wherein the nosecone has a luminal wall and at least one slot, and wherein the imaging transducer has 360° image capability of the vascular lumen through the at least one slot of the luminal wall of the nosecone.

9. The catheter of claim 1, further comprising a cam follower fixedly secured to the rotatable shaft adjacent to the proximal end of the rotatable shaft and configured for coupling with a cylindrical cam of a handle for use with the catheter.

10. The catheter of claim 9 in combination with a handle attachable to a proximal portion of the catheter, the handle including a power source, a motor connected to the power source, and a cylindrical cam configured for coupling with the cam follower secured to the rotatable shaft, wherein the motor is configured to transmit rotation to the cylindrical cam to both impart translation to the cam follower to move the cutting element from the stored position to the cutting position and impart rotation to the cam follower when the cutting element is in the cutting position to rotate the cutting element about its axis of rotation.

11. The catheter of claim 10, wherein the cam follower includes a projection and the cylindrical cam includes a spiral slot configured to receive the projection of the cam follower.

12. The catheter of claim 10, further comprising:
a controller having a body defining a lumen sized to accept the tubular body, the controller further having opposed body engaging elements within the tubular body for gripping the tubular body of the catheter, and a lever connected to at least one of the body engaging elements, wherein the lever is configured to move at least one of the body engaging elements from a disengaged position, in which the controller is free to move along at least the length of the tubular body, to an engaging position, in which the body engaging elements engage the tubular body to enable manipulation of the tubular body.

13. The catheter of claim 12, wherein the controller includes an activation member electrically connected to the power source of the handle for selectively supplying power to the motor, wherein the lever of the controller is configured to activate the activation member to selectively supply power to the motor.

\* \* \* \* \*